(12) United States Patent
Guillama et al.

(10) Patent No.: US 10,896,255 B2
(45) Date of Patent: Jan. 19, 2021

(54) DYNAMIC EPISODIC NETWORKS

(71) Applicant: The Quantum Group Inc., Lake Worth, FL (US)

(72) Inventors: Noel Guillama, Wellington, FL (US); Chester Heath, Boca Raton, FL (US)

(73) Assignees: The Quantum Group, Inc., Lake Worth, FL (US); Noel J. Guillama, Wellington, FL (US)

( * ) Notice: Subject to any disclaimer, the term of this patent is extended or adjusted under 35 U.S.C. 154(b) by 223 days.

(21) Appl. No.: 15/812,207

(22) Filed: Nov. 14, 2017

(65) Prior Publication Data

US 2018/0300476 A1 Oct. 18, 2018

Related U.S. Application Data

(60) Provisional application No. 62/421,879, filed on Nov. 14, 2016.

(51) Int. Cl.
| | |
|---|---|
| *G06F 11/00* | (2006.01) |
| *G06F 12/14* | (2006.01) |
| *G06F 12/16* | (2006.01) |
| *G08B 23/00* | (2006.01) |
| *G06F 21/55* | (2013.01) |
| *G06F 21/56* | (2013.01) |
| *G06Q 30/02* | (2012.01) |

(52) U.S. Cl.
CPC ............ *G06F 21/554* (2013.01); *G06F 21/56* (2013.01); *G06Q 30/02* (2013.01); *G06F 2221/034* (2013.01)

(58) Field of Classification Search
CPC ......... H04L 29/06904; H04L 29/06918; H04L 63/1433; H04L 63/145; G06F 2221/034; G06F 21/554; G06F 21/55; G06F 21/552; G06F 21/56; G06F 21/566
See application file for complete search history.

(56) References Cited

U.S. PATENT DOCUMENTS

| | | | | |
|---|---|---|---|---|
| 7,627,900 | B1 * | 12/2009 | Noel ................... | H04L 63/1425 709/223 |
| 9,532,295 | B2 | 12/2016 | Guillama et al. | |
| 10,178,120 | B1 * | 1/2019 | Keegan .............. | H04L 63/1433 |
| 2005/0257269 | A1 * | 11/2005 | Chari ................. | H04L 63/1416 726/25 |
| 2006/0085858 | A1 * | 4/2006 | Noel ................... | H04L 63/1433 726/25 |

(Continued)

*Primary Examiner* — Trong H Nguyen
(74) *Attorney, Agent, or Firm* — Nixon Peabody LLP

(57) ABSTRACT

A method for managing interactions and outcomes includes receiving data describing the propagation of a plurality of items through a system and modeling the propagation of the plurality of items through the system as a plurality of interconnected affinity groups. The method also includes identifying one or more undesirable affinity groups from the plurality of interconnected affinity groups. The method further includes, for each one of the undesirable affinity groups, performing the steps of: predicting at least one interaction required to cause at least a portion of the plurality of items associated with the one of the undesirable affinity groups to propagate to a desirable affinity group and causing the one of the undesirable affinity groups to interact with another affinity group configured to provide with the at least one interaction.

12 Claims, 16 Drawing Sheets

(56) References Cited

U.S. PATENT DOCUMENTS

| | | | | |
|---|---|---|---|---|
| 2006/0288415 | A1* | 12/2006 | Wong | H04L 63/1425 726/24 |
| 2008/0005555 | A1* | 1/2008 | Lotem | G06F 21/55 713/150 |
| 2014/0351154 | A1 | 11/2014 | Guillama et al. | |
| 2015/0067849 | A1* | 3/2015 | Agrawal | G06F 21/56 726/23 |
| 2015/0213202 | A1* | 7/2015 | Amarasingham | G06F 19/00 705/2 |
| 2015/0381649 | A1* | 12/2015 | Schultz | H04L 63/1433 726/25 |
| 2016/0378942 | A1* | 12/2016 | Srinivas | G06Q 40/00 705/2 |

* cited by examiner

| Assertion | Resistance | Field |
|---|---|---|
| Persuasiveness | Persuasion | beliefs and ideas |
| Infectious | Immunity | disease communication between individuals |
| Epidemic | Resistance | disease communication between populations |
| Propagation | Isolation | disease infusion within body |
| Efficacy | Inefficacious | pharmaceutical interactions |
| Opportunity | Failure | Marketing product need / acceptance |
| Leadership | Complacency | political concepts |
| Attractive | Repulsive | social acceptance / romance |
| Niche | Unfit | Ecological |
| Convincing | Implausible | Legal Dynamics / Jury Outcome / Legislative process |

2000

2050

DYNAMIC EPISODIC NETWORKS

CROSS-REFERENCE TO RELATED APPLICATIONS

This application claims priority to and the benefit of U.S. Provisional Patent Application No. 62/421,879, entitled "DYNAMIC EPISODIC SOCIAL NETWORKS" and filed Nov. 14, 2016, the contents of which are hereby incorporated by reference in their entirety as if fully set forth here.

FIELD OF THE INVENTION

The present invention relates to outcome management for a system, and more specifically to apparatus and methods for managing events in a system so as to provide preferred outcomes.

BACKGROUND

In the field of healthcare, it is often critical to know the source and potential progress of disease through the body or through a population. Increasingly, data bases are collecting information on health and medical parameters to the point where susceptibilities and immunities can be catalogued by individual. With such information, a computer has been used to assess the path of past infection or to predict the path of future infections. Such processes typically use simplistic models based on pre-defined assumptions. However, such models are typically generalized and thus imperfectly fit many scenarios. Accordingly, what is needed is a methodology that more accurately models infections.

SUMMARY

Embodiments of the invention concern systems and methods for managing interactions and outcomes. In a first embodiment of the invention, a computer-implemented method is provided. The method includes receiving data describing the propagation of a plurality of items through a system and modeling the propagation of the plurality of items through the system as a plurality of interconnected affinity groups. The method also includes identifying one or more undesirable affinity groups from the plurality of interconnected affinity groups. The method further includes, for each one of the undesirable affinity groups, performing steps. The steps include predicting at least one interaction required to cause at least a portion of the plurality of items associated with the one of the undesirable affinity groups to propagate to a desirable affinity group and causing the one of the undesirable affinity groups to interact with another affinity group configured to provide with the at least one interaction.

The method can also include the step of, after the causing, repeating the modeling, identifying, and performing until at least one criteria is met. The at least one criteria can include a number of the plurality of items in the one of the undesirable affinity groups propagating to the desirable affinity group exceeding a threshold.

In the method, the plurality of items comprise a plurality of computing devices and one or more items of malware, and wherein at least one of the undesirable affinity groups includes the at least one of the items of malware.

In the method, the modeling can include simulating the propagation using an initial set of parameters and the repeating can include updating the set the parameters prior to repeating the modeling, identifying, and performing. The updating can include comparing properties of the undesirable affinity groups to properties of one or more reference groups, and estimating changes for the set of parameters based on the comparing.

In a second embodiment, there is provided a system comprising a processor and a memory. The memory has a computer program stored thereon for causing the processor to perform the method of the first embodiment.

In a third embodiment, there is provided a non-transitory computer-readable storage medium having stored thereon a computer program for causing a computing device to perform the method of the first embodiment.

BRIEF DESCRIPTION OF THE DRAWINGS

FIG. 12 is a table of assertion and resistance pairs and related fields that is useful for understanding the various embodiments;

and

Figure 19A:
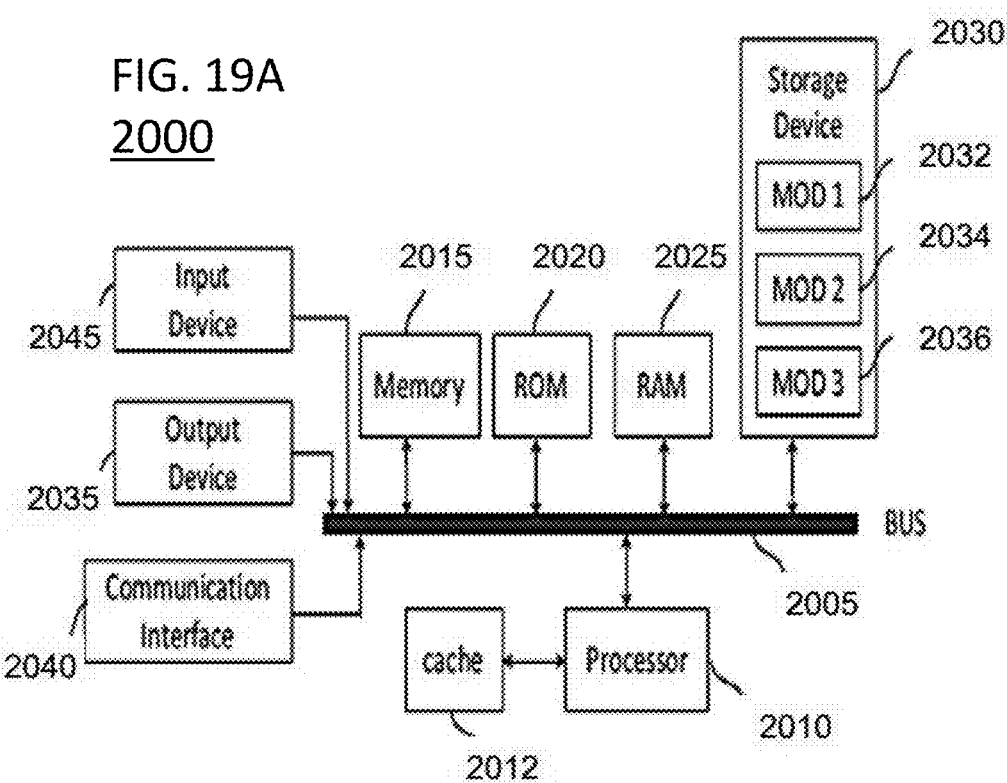
Figure 19B:
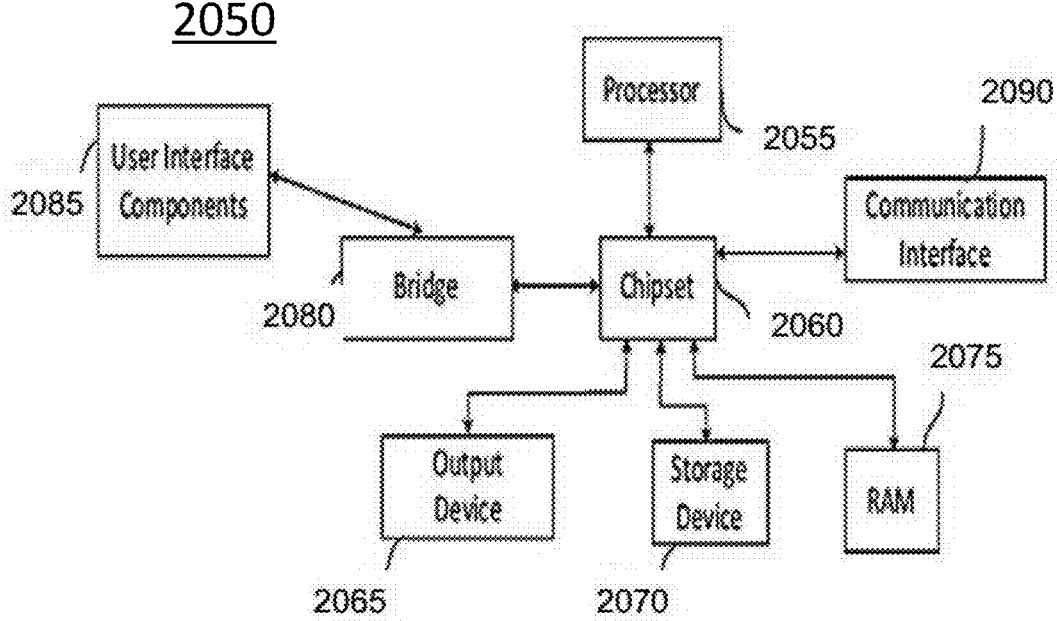

FIGS. 19A and 19B show an exemplary computing system for implementing the various embodiments.

DETAILED DESCRIPTION

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The various embodiments build on the concepts of Episodic Social Networks (ESNs) described in U.S. Patent Application Publication No. 20140351154A1.

The various embodiments are directed to systems and methods for identifying influential interactions or contests within a system and managing outcomes in the system by studying the effects of such interactions or contests on the individual components of the system. For example, by studying the interactions of the components of a system at an individual level using iterative process. By predicting the contests between components at the individual level and comparing iterative exercises to the actual outcome, then the presumed dynamics of the contest can be determined from the "best fit" exercise. Potentially, the division of population (potentially into separate affinity groups) can then be predicted. Where the beginning and end points of an infection are known, the susceptibilities and resistance of the involved components can be estimated. Relative to disease, infection, epidemiology and pharmaceutical efficacy, this has a potential for use when tracking or predicting disease communication where known specific identities have high potential for transmission or reception. This could be an effective tool—and useful in other fields as well. Indeed, current affinity groups could be defined from social networks where there is consistent communication.

Rather than simple probabilistic simulation, the various embodiments are directed to means that can determine the parameters of contest between individuals and then use those parameters to calculate the outcome of a contest in a predicable manner. That is, it is a means by which past and future disease processes can be demonstrated or predicted. The concept should have broad application in healthcare, epidemiology, pharmaceutical and other fields as well. The various embodiments could be useful in selecting and allocation of medical resources where most effective in triage situations. Further, knowing the parameters of infection for large groups of individuals could assist greatly in communicable disease abatement, homeland security and military applications especially. In the various embodiments, the speed and accuracy of a computer needs to be leverage in order to evaluate potentially large datasets within a reasonable amount of time.

Figure 1:
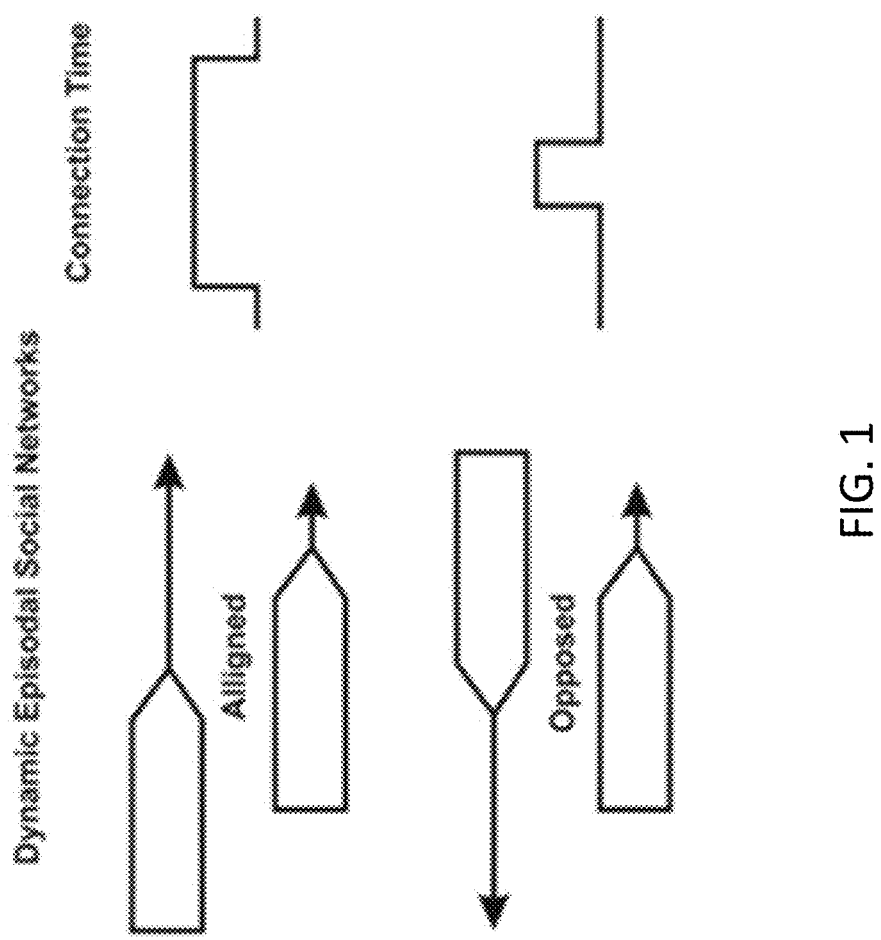
FIG. 1 is a schematic that is useful for understanding the various embodiments.

It is generally accepted that the degree of communication is dependent on exposure time and communication effectiveness or alignment. This is illustrated in FIG. 1, which shows schematically that when communication is aligned (top left), the connection time or effectiveness is lasting (top right). In contrast, FIG. 1 also shows when communication is not aligned or at cross-purposes (bottom left), the connection time of effectiveness is limited. Thus, effective communication is not just dependent on exposure time, but also as receive and transmission efficiency.

Figure 2:
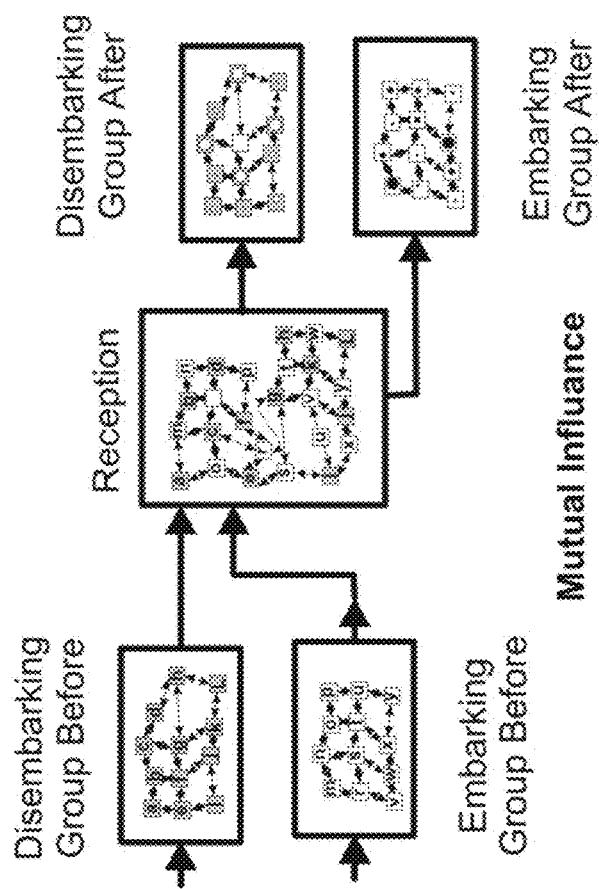
FIG. 2 is a schematic that is useful for understanding the process of mutual influence in accordance with the various embodiments.

An analogy to introduce this concept is shown below with respect to FIG. 2. A Yucatan cruise line wishes to increase the subscriptions for optional side trips to Aztec temple archeology and Scuba-Snorkeling (two choices). To influence the selection, the cruise line implements a reception. A dozen people disembarking join a reception for a dozen people embarking, who have not yet chosen their side trips. The expectation is that the disembarking passengers will influence the choices of the embarking passengers by word of mouth. A questionnaire has asked the disembarking passengers to rate the side trips in a scale of 0, 1, 2, 3. And embarking passengers have already requested priorities as to which side trips they want, based on expectations and requesting a priority of 0, 1, 2, 4.

Figure 3:
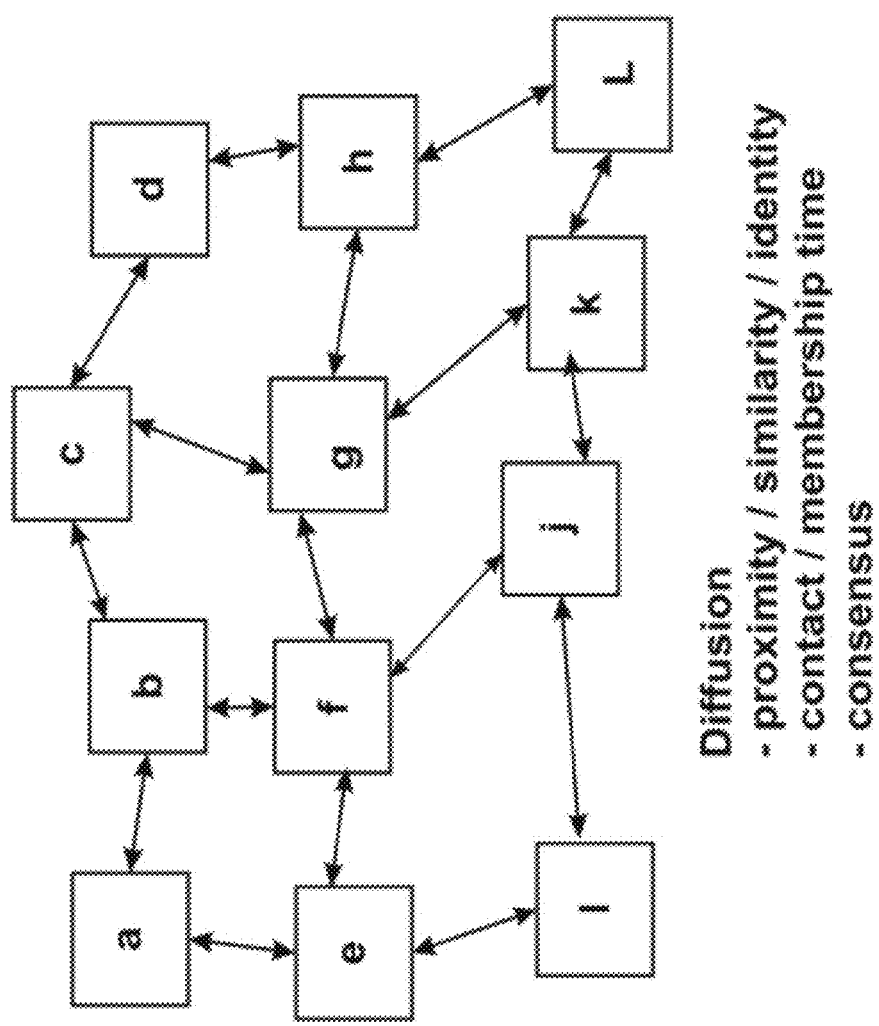
FIG. 3 is a schematic that is useful for understanding the process of diffusion in accordance with the various embodiments.

However, after the reception, embarking passengers get to change their priority. Disembarking passengers are offered a discount on side trips if they elect signing on for a future cruise. So, each one of the 24 people can influence future choices of the 23 others. The opinions diffuse through the group as disease might through a body or population. For example, as shown in FIG. 3, opinions might diffuse through interactions, despite each individual interacting with only a portion of the group. Assuming that it is possible to rank each individual according to their persuasiveness and their susceptibility to word of mouth (person to person) influence and predict how each person will be influenced by a mathematical/logical calculation.

The problem is analogous to disease communication and solvable with the aid of modern data processing. How many calculations are required to make this prediction? The number of combinations that have to be calculated is surprisingly small. But even if it were 1000 times larger—these are not operations that are beyond workstations and clustered servers as calculators. The calculations are like those required in computer animation, or encryption, or compression in that respect.

In the various embodiments, an iterative program of finite steps is provided to "weigh" the effect or influence of each interaction. However, a question might be how many iterations are required. Fundamentally, it is a function the number of potential interactions and the number of choices.

Therefore, if one substitutes "degree of infection" for "persuasiveness" and "efficiency of the immune system" for "susceptibility", one can then begin to model the modality and direction of infection with this process. These are parameters that can be accurately measured. The size of the calculation is related to the practicality of using this process in real time:

$$\frac{n!}{r!(n-r)!} = \binom{n}{r}$$

is the number of interactive combinations, where n is the number of things to choose from, and one can choose r of them. Thus, in a simple example:

$n=24$ $r=4$ (1 of 4 choice of 0,1,2,3)

then $r! = 4! = 24$ $$(n-r)! = 20! = 2.432902008$$
$$E+18 = 2432902008176640000$$

and $$n! = 24! = 24 \times 23 \times 22 \times 21 \times (20!) = 255024 \times (20!)$$

Reducing the Calculation $$\frac{24!}{24 \times 20!} = \frac{23!}{20!} = \frac{23 \times 22 \times 21 \times (20!)}{20!} = 10626$$

Even with iterative steps of 1000 instructions per step—this sounds reasonable—roughly 10 million instructions per second.

Figure 4:
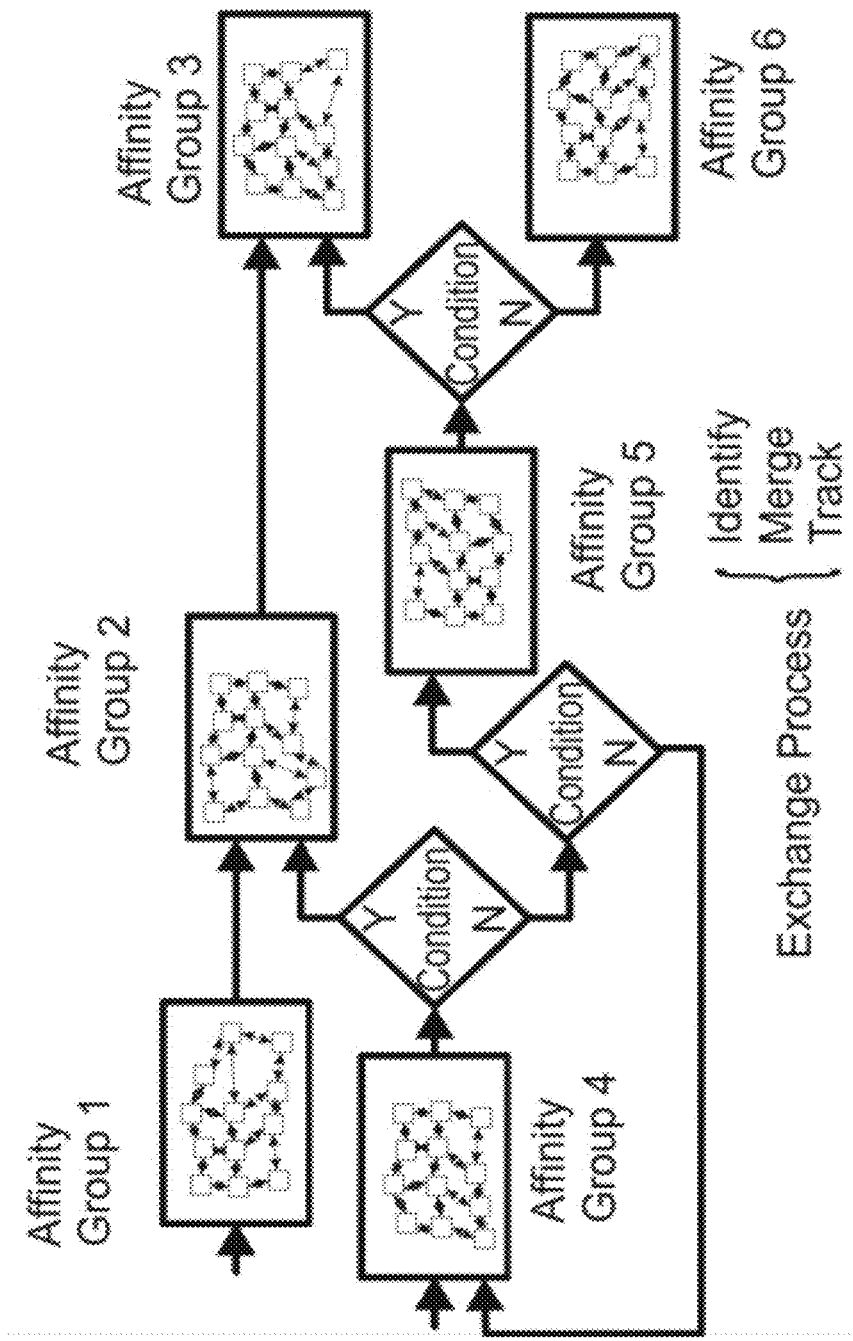
FIG. 4 is a schematic that is useful for understanding an exchange process in accordance with the various embodiments.

Referring to prior submission on ESNs, the concept is here extended to allow for interaction and influence within the group. This is illustrated in FIG. 4. Where an individual may migrate from one group to another at a decision point, individuals may be persuaded, or infected, within a group in the interim. A decision point might be a diagnosis for example, where the information guiding the decision point incubates within some members of a group.

Figure 5:
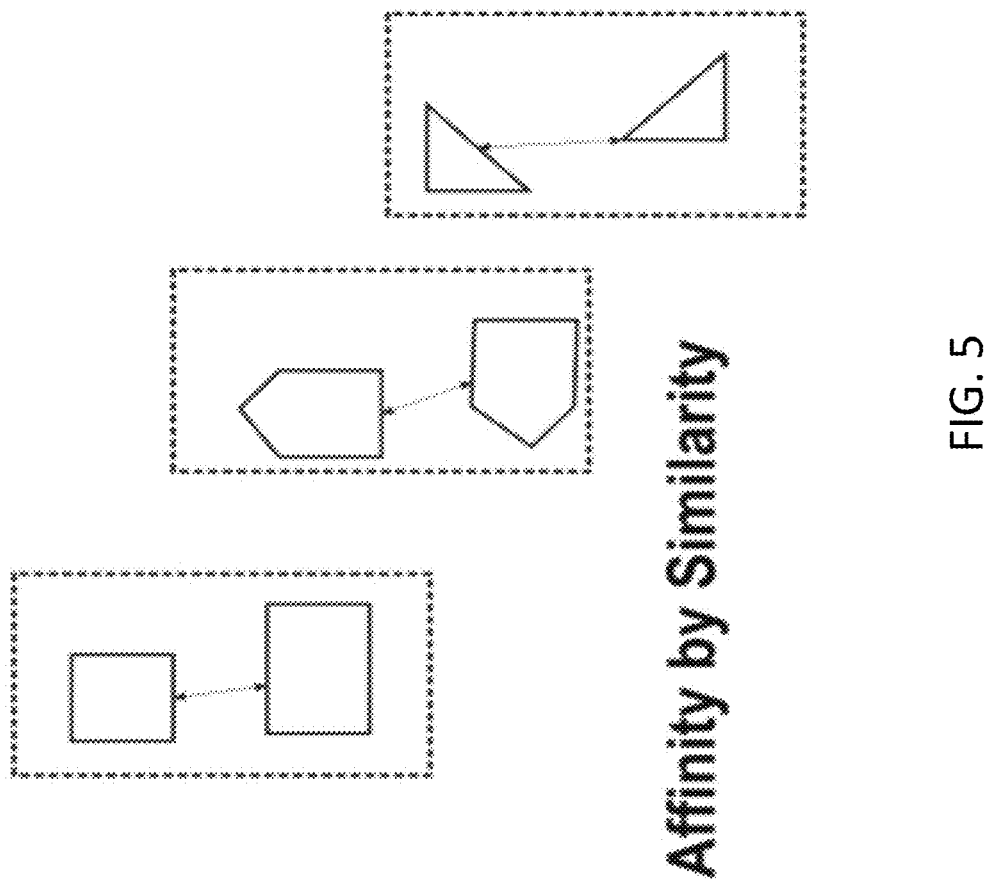
FIG. 5 is a schematic that is useful for understanding affinity in accordance with the various embodiments.
Figure 6:
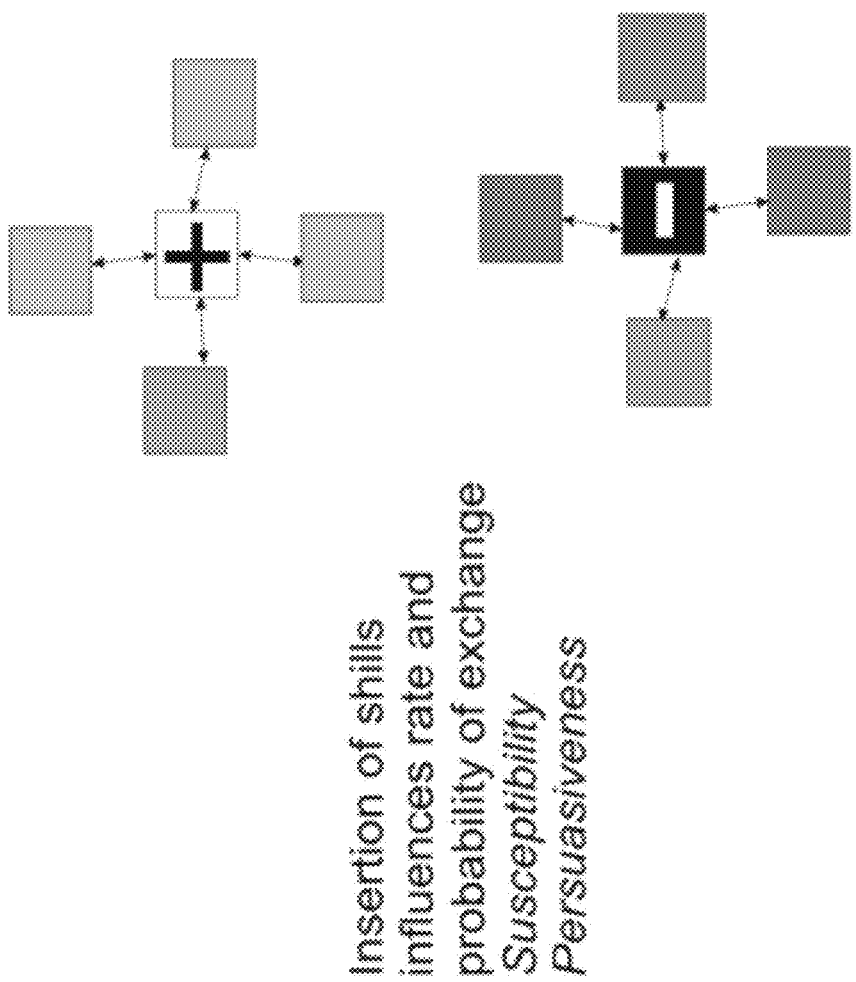
FIG. 6 is a schematic that is useful for understanding shill influence in accordance with the various embodiments.

Indeed, when one population (affinity group 1) is joined or infused by another population (affinity group 2) there is communication that is modulated by the exposure time, susceptibility and communicability of the members. This is what happens when one group (the embarking affinity group) is joined in the reception by the disembarking group. Not only do they infuse each other with their opinion and expectations surrounding the cruise—they can in an analogous fashion infect each other with a communicable disease. Within the body, these may be different organs infusing an infection by proximity or blood/lymph flow. Within a group, communication may also be aided by the similarity of the components that become associated, as illustrated in FIG. 5.

Continuing the analogy, if the cruise line were to insert shills or other biased individuals into the reception, the outcome could be diverted, away from, or toward a goal, depending on the efficacy of the argument afforded by the shills. The shills might speak effectively of local criminal activity near the architectural tour, or reported sharks in the area of the diving. This would be analogous to disease promotion attributes or interruption attributes, such as antibiotics within a body. Fewer or lesser individuals might join the diagnosed group.

Figure 7:
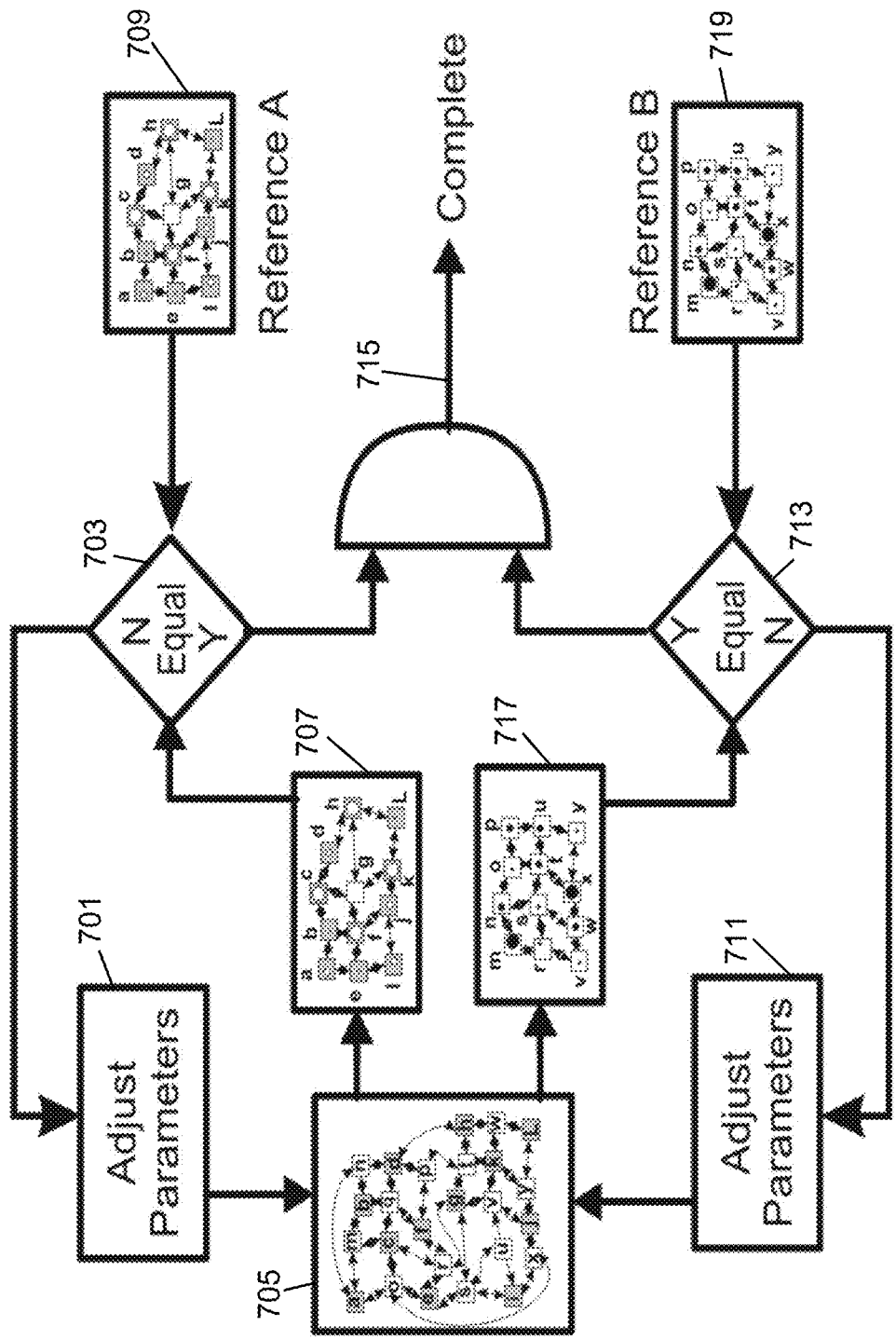
FIG. 7 is a flowchart describing the iterative process of estimating the susceptibility and persuasiveness of individuals in a mixed group illustrating a method used in accordance with the various embodiments.

Thus, in the various embodiments, determining the process of infection (of opinions in the analogy) or disease in the healthcare application, would be an iterative combination of components, where the adjacent components, or similar components, of known susceptibility and infection communicability are tested as follows:

In particular, each individual interaction is considered a contest. With reference to FIG. 7, as an expansion of the process shown in FIG. 2. First, a mixed group 705 is identified and processed according to parameters 701 and 711. For example, such a mixed group can be formed from individuals of two (experienced and non-experienced) groups potentially exchange (an opinion, experience, disease, etc), with the parameter 701 and 711 setting forth how the mixed group interactions. In terms the first cruise line example, the mixed group can consist of the embarking and disembarking groups. As in FIG. 2, if a person, who has been exposed to an experience (or disease) is more persuasive (or infectious) toward an inexperienced (or unexposed) person, who is more susceptible to argument or opinion (disease), their opinion is likely to change—the opinion or disease is thereby infectious. Thus, at the end of the interaction, the group 705 splits into two groups 707 that is infected (or persuaded) and another group 717 that is not.

This same process applies to processing computer files. That is, the mixed group can consist of a set of files including infected (by a virus or other malware) and uninfected files. These files can then interact or be processed in a computer system, according to parameters set forth in 701 and 711. Based on the processing (i.e., the interaction), the mixed group 705 results in two sets of files, infected files in group 707 and uninfected files in group 717.

In the process of FIG. 7, the end goal is to simulate all possible interactions as parameters of persuasiveness 701 and susceptibility 711 in order to minimize or maximize groups 707 and 717. Every possible interaction within the group 705 is simulated, iteratively, by adjusting the parameters 701 and 711. The results (i.e., the constituents of groups 707 and 717) are compared at 703 and 713, respectively, to Reference A 709 and Reference B 719, respectively. A correct set of parameters 701 and 711 is them found when the outcome (groups 707 and 711) substantially matches Reference A 709 and Reference B 719. In the various embodiments, the matching can be a matching of properties or other criteria of the reference groups and the outcome groups. However, in other embodiments, the matching can be a target result. That is, a desired set of constituents or members in particular groups.

Based on this result, the parameters 701 and 711 can then be used to create a desired outcome with mixed groups. Alternatively, the parameters 701 and 711 can also be used to rank or classify the susceptibility and persuasiveness of each individual or constituent of a group. Particularly, from perspective of public health, with communicable disease, it is desirable to indentify, those who are less and more resistant as potential victims or carrier of infection.

Figure 8:
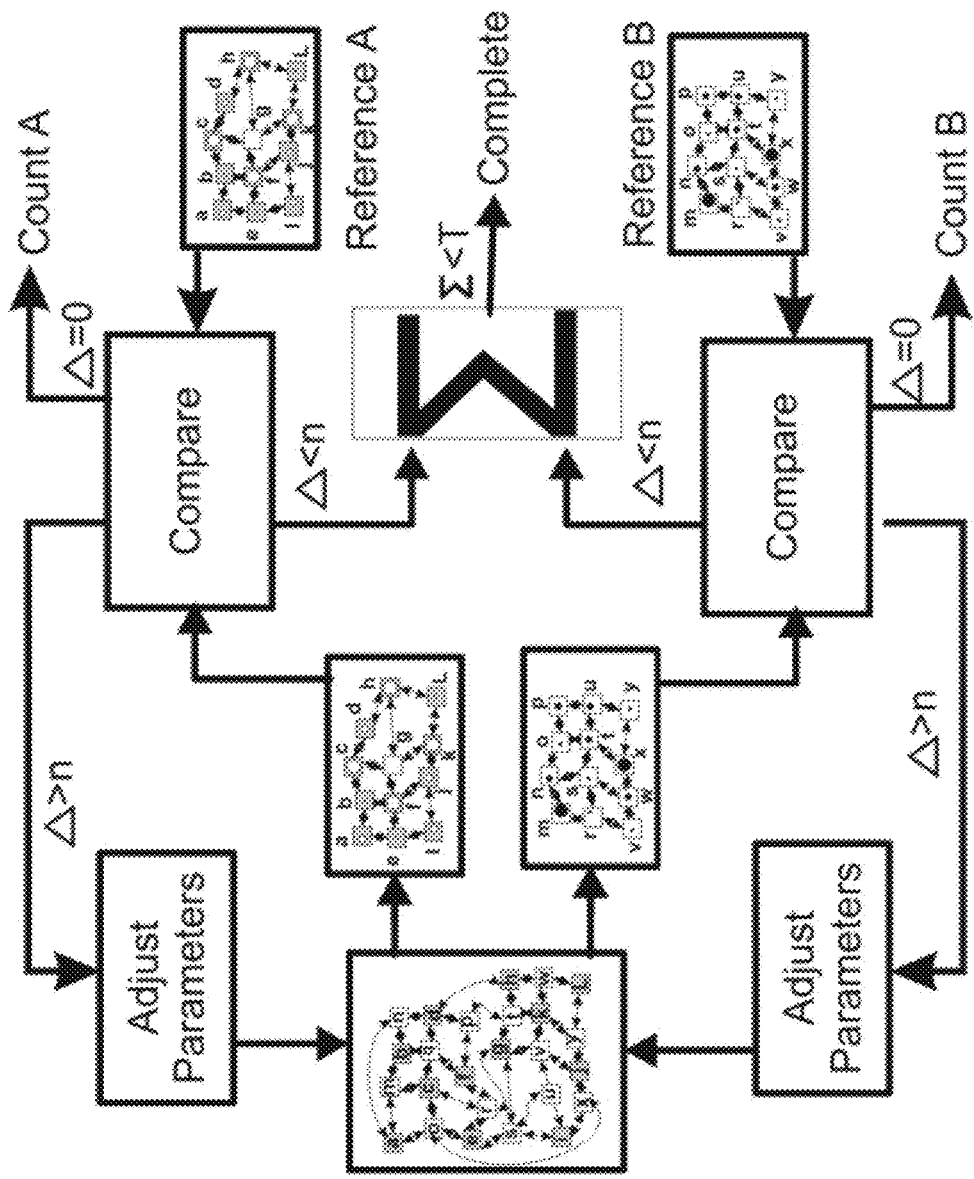
FIG. 8 is a similar flowchart describing the iterative process of estimating the susceptibility and persuasiveness parameters as variable values of individuals in a mixed group illustrating a method used with numeric comparison in accordance with the various embodiments.

FIG. 8 describes essentially the same process as FIG. 7, where the parameters are more refined numeric values and the comparison becomes a more exact numeric process. This information would of course be stored in a HIPPA compliant Electronic Health Record facility.

In the various embodiments, the process is repeated for every potential degree of susceptibility and communicability if those parameters are unknown (from a healthcare database) at the onset. By this means, when a best fit scenario is calculated, from a past episode of communication, then degrees of susceptibility and communicability can be inferred and recorded by each individual for later use. Theoretically, this process could also catalogue all individuals as a healthcare database grows.

The same process could be used to evaluate the persuasiveness and susceptibility to advertising, word or mouth communication, social network interaction. Indeed, a social network could be mined for these interactions to determine who the influencers and followers are within a social group. This would be especially useful in marketing of products, political opinions or candidates, or predicting the future preferences of the influencers and followers.

The process is prohibitively excessive for human calculation, but containable within the capabilities of a computer. As previously shown, where the parameters of susceptibility and communicability to a disease (or opinion) are known the number of calculations is finite. Where all degrees of combination are exercised for unknown susceptibility, the process is much larger, on the order of 24 factorial, but still containable within the capabilities of a supercomputer within a reasonable amount of time for the calculation. One can imagine that the capabilities of supercomputers, which have followed Moore's law of doubling every year or so, will be able to encompass very large groups indeed.

The process can of course be accelerated by specific hardware, or hardware instructions, defined for a computer that is specifically designed for the purpose. Here there are registers for each individual and hardware comparison, where each combination can then be executed in parallel by iteration. The operation is complete when the calculated outcome closely resembles the actual (reference) outcome, another measure might be when the count of comparison exceeds some threshold of desired accuracy. That is:

If State is 2-bit value but the 2MostSigBits
and N<24 then $\Sigma$<T is the acceptable Error Threshold
effectively an estimate
Alternatively scan for greatest number exact (compare=0)

Figure 9:
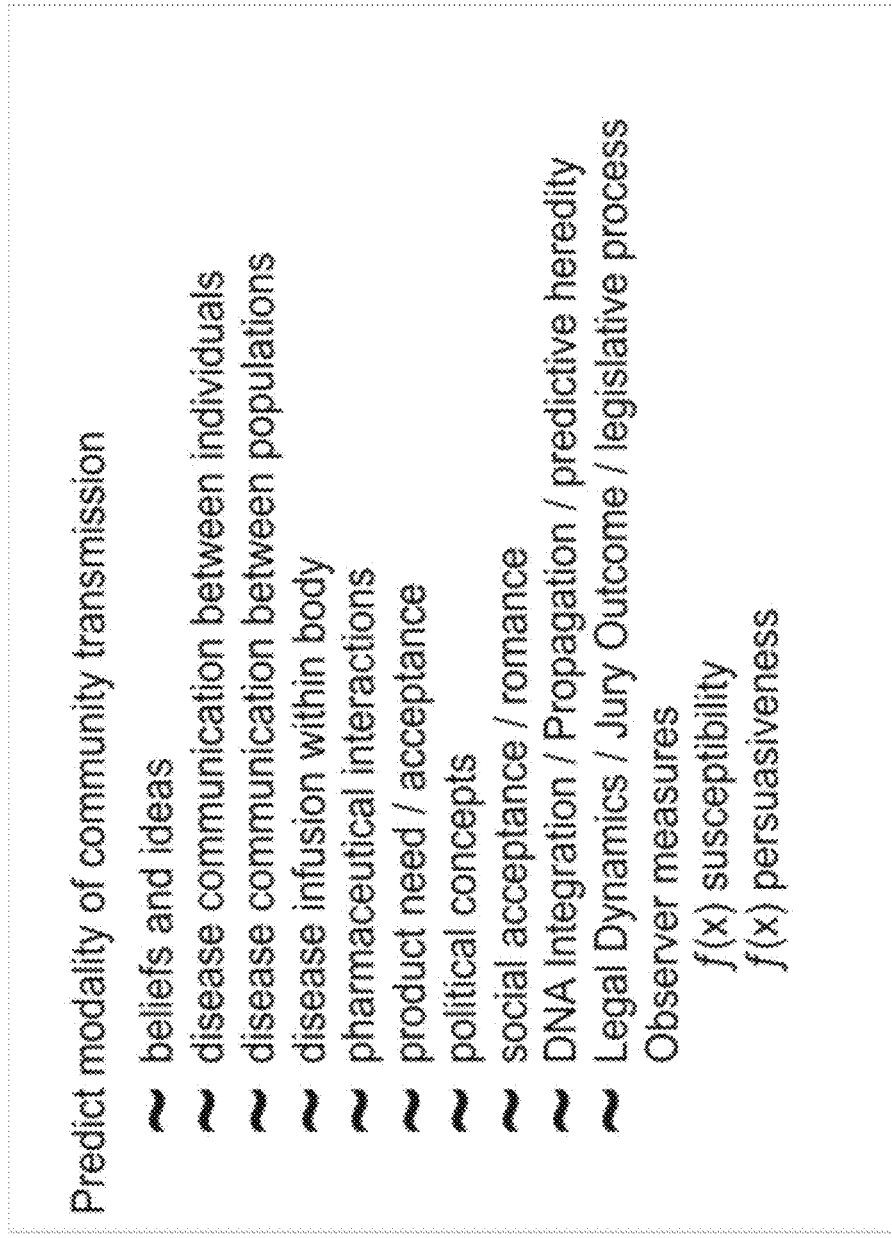
FIG. 9 is a table of modalities that can be addressed by the various embodiments.
Figure 10:
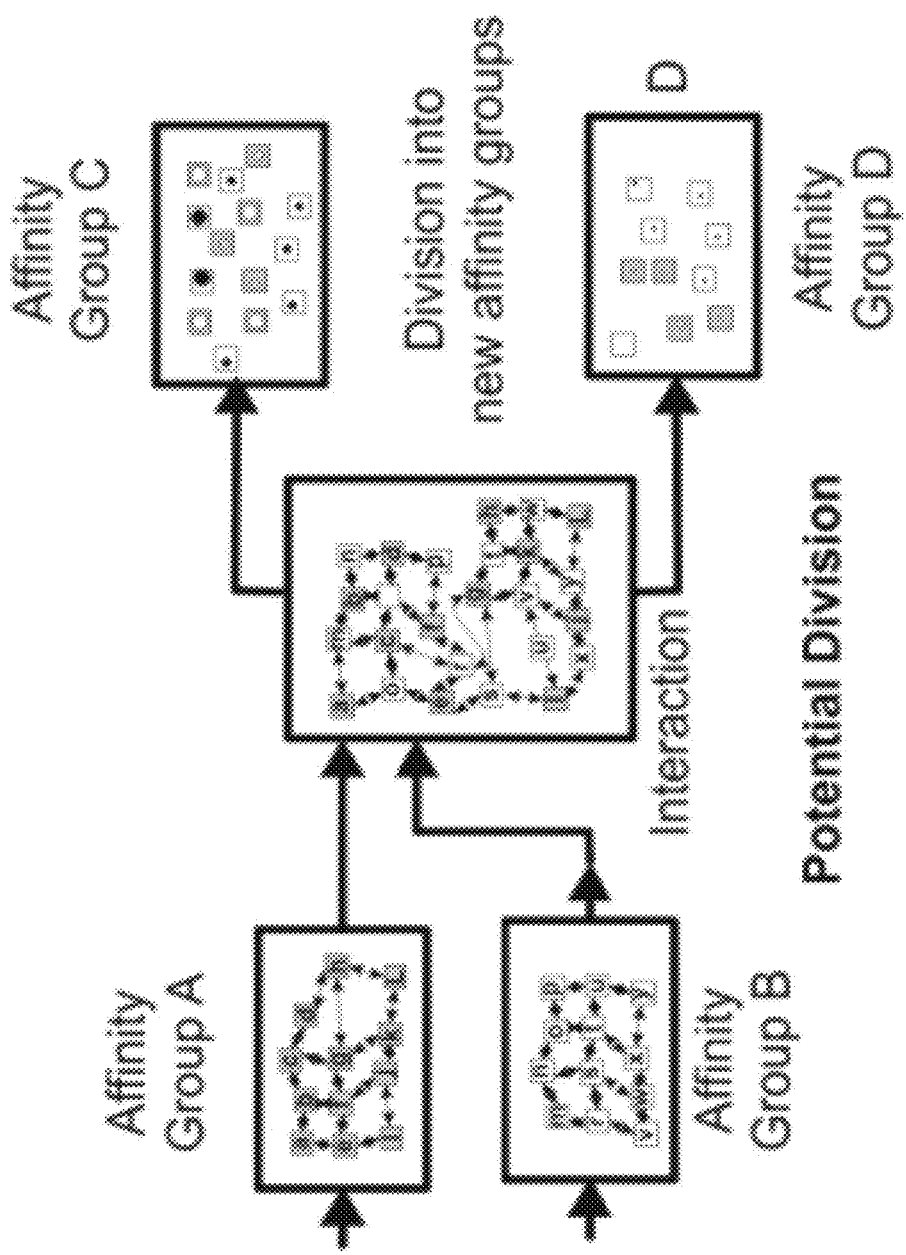
FIG. 10 is a schematic that is useful for understanding division of affinity groups in accordance with the various embodiments.

This means is proposed primarily as a means for tracking and predicting the path of infection for healthcare, but utility is also seen in other fields of study:

Yet, as shown by the initial analogy, there is potential for tracking word of mouth recommendation, to form opinions, beliefs and ideas. This has great utility in marketing to determine the potential need and acceptance, or rejection) of product ideas as perhaps tested by focus groups of sufficient size and known statistical validity for extrapolation. Some examples of such interactions are shown in FIG. 9. Political concepts and contests could be exercised such that ideally ethical politicians might more effectively implement the will of the people in a lasting way. There is potential in pretesting individuals or groups for affinity, the objective might be a dating website's accuracy, a jury's fairness, or if a given military group can be defined for maximal effectiveness under stress in battlefield conditions. Indeed, if the parameters of susceptibility and communicability ("persuasiveness" and "susceptibility") are known, or can be estimated from past exercises on known individuals, then the ability to indoctrinate, convince or radicalize groups toward action, e.g. terrorism, religious fervor, or revolution might be calculable. If the parameters of persuasiveness and susceptibility are determined, then many more forms of human interaction can be calculated. Such a process is illustrated in FIG. 10.

Affinity groups may re-organize as a result of contests—members of the scuba group trade places with members of the archeological group. Members of a group may conquer one disease, yet become susceptible to another as a result of treatment. E. g. anti-cancer infusion may cure the cancer, yet create a susceptibility to heart disease. In this fashion, Dynamic Episodal Social Networks become sequential and operate are originally defined.

Figure 11:
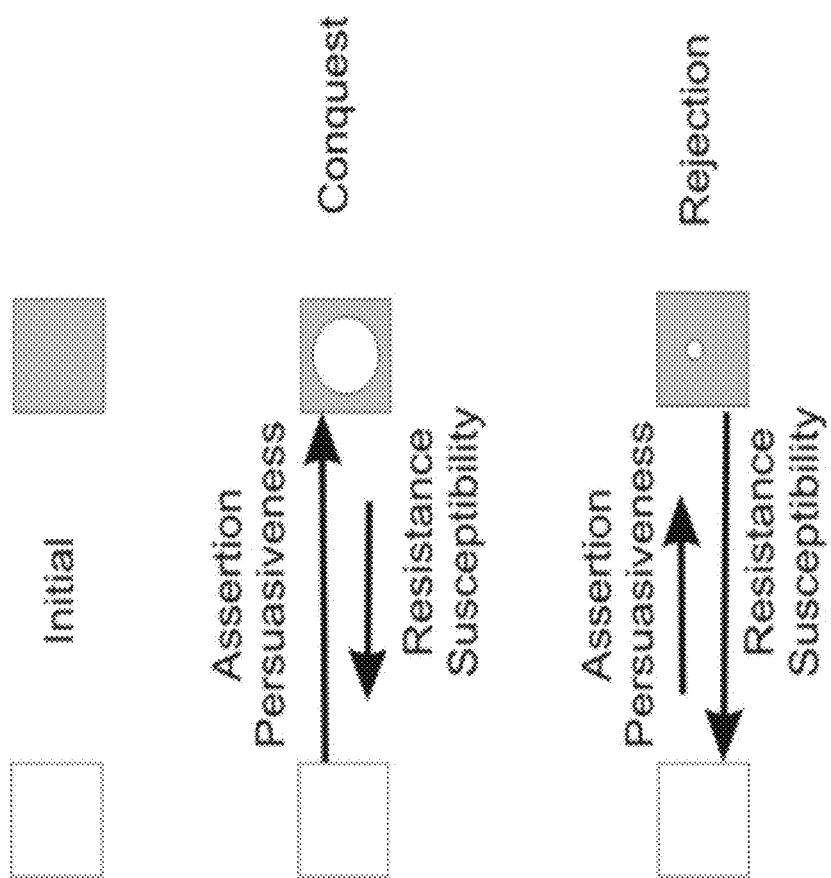
FIG. 11 is a schematic that is useful for understanding the effect of interactions on outcomes in accordance with the various embodiments.

An affinity group may also reach equilibrium where the contests stabilize. This is illustrated in FIG. 11. And taken as a discrete entity, the affinity group may act as an individual. For example: Assuming that only one side trip is possible, will they vote for the archaeology tour or scuba, guilty or innocent, violence or diplomacy, surrender or annihilation. There is a contest of assertion, versus resistance that is applicable to many fields. Examples of such assertions, resistance, and applicable fields are shown in FIG. 12.

Additional Embodiments

Generally, the various embodiments apply to wherever one needs to provide a means to enable, prevent, or predict propagation of communication, where delays in action for the decision process are acceptable. Outside of healthcare, there are many alternative embodiments, especially towards the technical side, where a means for evaluating the extended contest of assertion, versus resistance applies.

Generally, a method in accordance with the various embodiments could be used to calculate an outcome confidence level using majority rule decisions at termination of interactions within an affinity group. There may many different alternatives, which superficially appear similarly probable, where one alternative may yield a higher confidence score after the interaction of peers in such a contest. For example: At the end of an interactive educational experience, which individuals will most likely pass entrance exam threshold for a given direction. Extending the concept a bit—which peers would you accept into the educational experience, such that the most promising individual is developed. This may not be the most promising individual at the onset, but the one who grows the most, benefits the most from the process of interaction between peers.

Similarly, a method in accordance with various embodiments could refine alterative maps of an ESN to determine which is most real, most likely, most productive. It may be used as a data mining technique, where once a set of parameters are known for a few, then the process rerun with n known and (total−n) unknown individuals. At points within the dynamic ESN, seed or bias to create additional matching exercises could be defined.

Specific Examples (1) An IT group wishes to optimize Anti-virus control and intrusion potential in an organization. Knowing that each system may have a different mix of applications, each with differing susceptibility to infection and communicability to other systems. You can use the method to predict how the virus may most probably spread and target weaker system points to control how and where it propagates.

Figure 13:
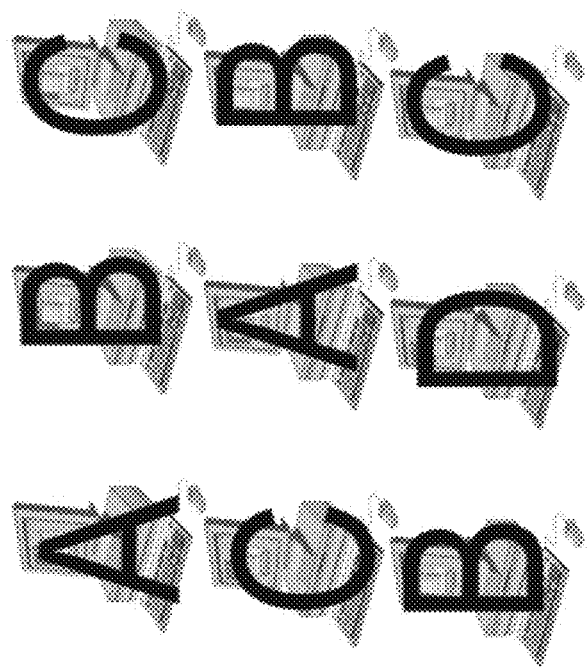
FIG. 13 is a schematic that is useful for understanding an exemplary embodiment.

Some systems may be more susceptible by the applications that they use, because those applications are more generally deployed and are more uniform in their design. For example, a browser may have design vulnerabilities and using it uniformly might assist the propagation of a given virus through a network. Knowing the weaker points of the system would dictate a different browser for that system. Indeed, a mix of multiple browsers, as shown in FIG. 13, may be the best solution, such that—knowing the most probable paths of infection—the least virus communicability can be defined for the systems that are most probable for transmission.

Figure 14:
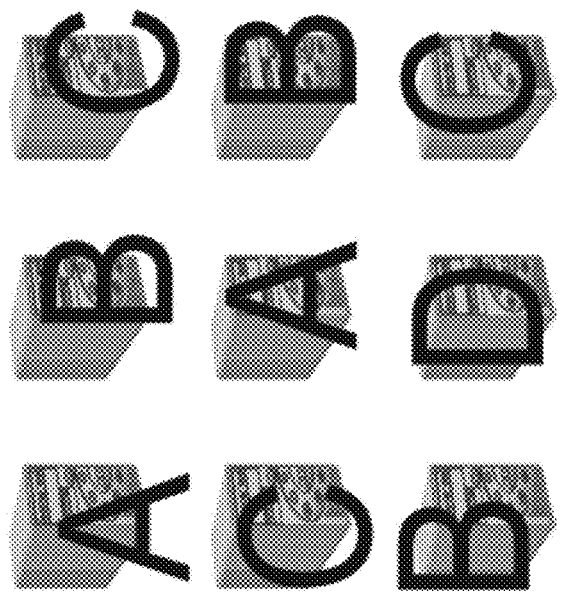
FIG. 14 is a schematic that is useful for understanding an exemplary embodiment.

This would be especially useful in protecting a data center. An array of servers is often a sitting duck for a rapidly communicating virus, or for external (or internal trusted worker) intrusion. One might protect each server with its own router/firewall. However, if all firewalls use the same software, and a virus or intrusion attempt is designed to focus on that software, individual firewalls might provide less protection. Knowing the weaker points of the system, and the servers most likely to intercommunicate, and/or the more critical servers to protect, a mix of firewall programs, as shown in FIG. 14, could be deployed in a matrix to best thwart internal propagation of such a virus.

Additionally, some servers may be more critical, or more central to operations, such that if virus or intrusion is detected on one firewall, it may alert others to block communication to stop the spread of the virus, or intrusion attempts. Those other servers and firewalls, would be specifically selected by the above technique.

In the healthcare analogy, this would like to inoculate the more critical medical workers, fire and police and the more susceptible young and elderly first. Further, teachers and daycare workers and assisted living providers might be also on the list, because they are more frequently in contact with the more susceptible individuals. Indeed, the blocking of communication to prevent the spread at specific firewalls is analogous to selective quarantine.

Figure 15:
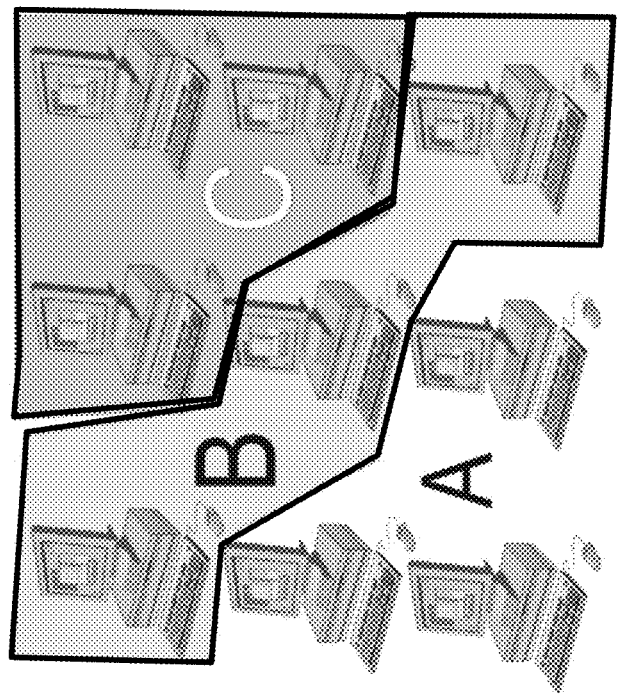
FIG. 15 is a schematic that is useful for understanding an exemplary embodiment.

(2) In a relative sense, software or database updates are also managed by an IT organization. When deploying updates across an organization, or even a population, a large number of them might occur at the same time. As a result, servers and networks can be easily overloaded. With the invention, you can actually allow and encourage specific delays in update deployments. For example, the SW update strategy would be to identify the relative priority of devices for performing the updates and encouraging updates on the higher priority devices and discouraging updates on the lower priority devices. Updates could be deployed in stages, such that more susceptible and critical systems might receive changes last to allow less critical systems to exhibit problems first (not all updates are perfect; some actually impair operation). However, once an update is known to be effective and/or less problematic it might then be installed first on more critical systems. This is illustrated in FIG. 15.

This would be similarly useful in healthcare for deployment of inoculations, which are indeed, software updates to the immune system. Or it may be used to deploy new medicines to individuals, groups, even societies that are most critical. Indeed, the field trial subjects of new medicines may be selected by the above technique as well.

Figure 16:
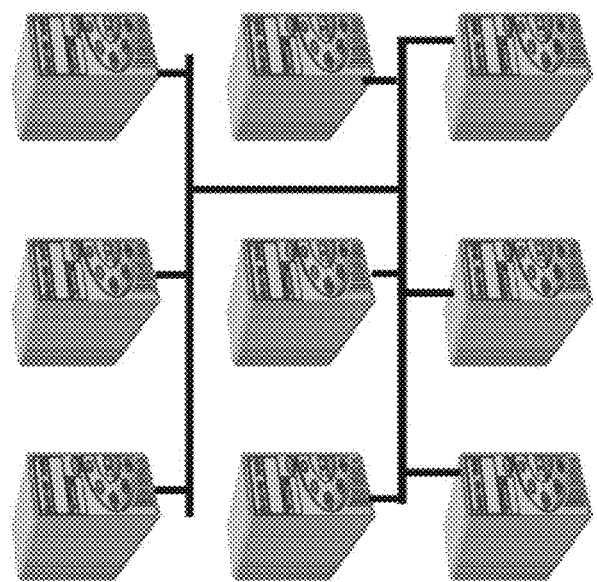
FIG. 16 is a schematic that is useful for understanding an exemplary embodiment.

(3) Internet traffic control. In a large backbone or grid, there are also susceptible and critical components. Indeed, a major concern of Homeland Security is the vulnerability of specific elements of a network: those that communicate the most, those that are single points of failure, those that are vulnerable points of intrusion and those that are more probably overloaded. This invention provides a means to identify and protect those systems—by identifying the susceptible and resistant nodes to infection in a network. FIG. 16 shows several servers in a data center, where it is commonplace for many servers on the same network to become infected and in turn infect others. As in FIG. 15, some of the servers are unprotected and depend only on the perimeter security of the data center. Other servers have a software firewall upgrade that gives them some protection against intrusion and infection. A few have individual hardware firewalls, with hardened internal software, that are much more difficult to defeat.

The servers also may have various content, with some carrying financial data, others carrying pornography, and others with health data. Depending on the potential interactions, susceptibility of a given server and persuasiveness parameters of potential intrusive software, the more vulnerable servers can be determined by this means.

(4) A related situation is the propagation of information via torrents. There may be no central server systems and every recipient becomes a donor to other recipients. It is much like the pot-luck dinner, where everyone exchanges their component of a meal. There is no common server, each participant exchanges what they have available. This reduces a centralized server load, when it is components of a larger file that are being exchanged, but creates a potential congestion problem generally on a network as a very complex assortment of torrent partners announce what pieces they have, what pieces they need or provide pointers to others where torrent data may be found. This is an open conversation between systems that is directly comparable to the initial example of mutual influence in embarking and disembarking cruise ship passengers.

(5) Roadway Traffic control. In a large urban area, traffic during rush hour is also a complex exchange. Many drivers tend to use Waze, Google maps, or the like navigation tools to get around. However, if a group of users is heading to a same destination and currently at a same location are looking for the shortest route at rush hour. When all users shift to the shorter route, or faster route or most use of freeways route, in a collective sense, these programs might exacerbate the very congestion problem that they aim to solve. If you are simply moving the traffic from one route to another and just moving the gridlock there, or some point in between.

Figure 17:
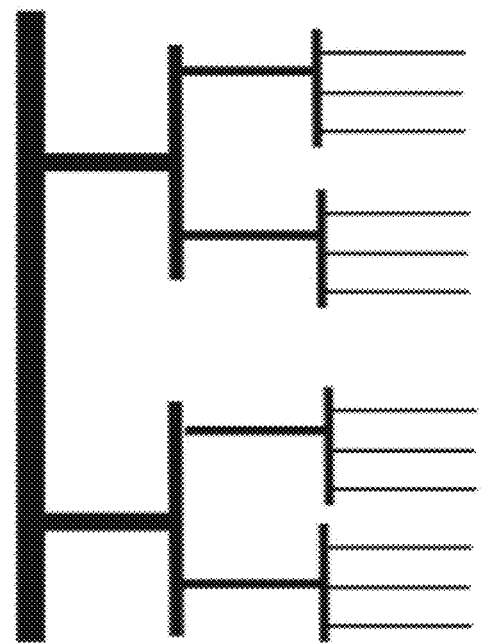
FIG. 17 is a schematic that is useful for understanding an exemplary embodiment.

One could use an embodiment of this the invention to balance out the directions to all users in a way to ease traffic and help all travelers. For example, referring to FIG. 17, if you have X users on the interstate going to the same location, a first alternative route that shaves 2 minutes off the trip, a second alternative route that shaves 4 minutes off the trip, and the system allows for up to a 5-minute delay, the system would encourage a ⅓ of the users to use alternate route A, another ⅓ of the users to use alternate route B, and a final ⅓ remain on the interstate (I). The net effect would be that (1) you remove traffic from the interstate, hopefully helping those left behind and (2) you wouldn't dump all the removed traffic into one single route so as to minimize or at least not cause delays on such routes. (First Do No Harm).

Figure 18:
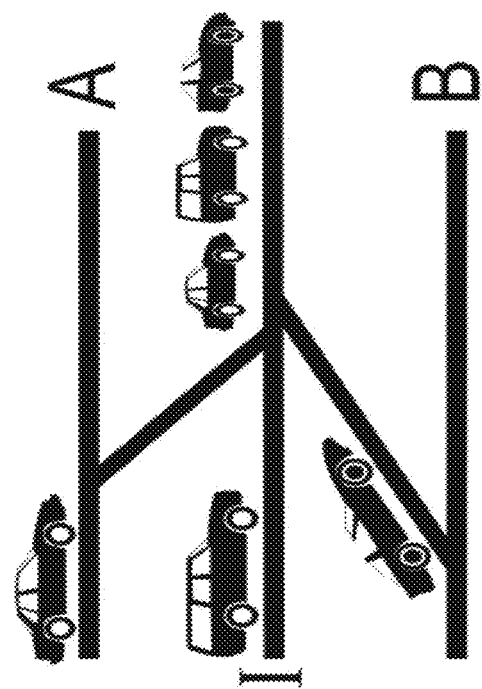
FIG. 18 is a schematic that is useful for understanding an exemplary embodiment.

(6) Similarly, such a strategy could also be used to control traffic on communications networks, in a scalable sense, such that blockages would not be passed laterally (as in the above rush hour traffic example) but also vertically (as illustrated in FIG. 18) as small networks feed larger networks, backbones or up to national grids and international satellite communications. The concept could also be defined for distribution of power in grids, or power management in buildings or neighborhoods to minimize peak load on the distribution means.

(7) Logistics and distribution of goods. Shipment by rail, air, truck can produce predictable bottlenecks, were a means similar to rush hour traffic optimization above could reduce interactive loading on a highway, airport or rail system. Indeed, where materials are shipped by multiple means, as in the combination of UPS and Postal service cooperative shipments, congestion could be avoided at the points of transfer as well as the routes within one network.

(8) Predictive Path Propagation Control—in U.S. Pat. No. 9,532,295, knowing the schedules of multiple vehicles, an optimal sequence of passage of information between vehicles to effect a longer-range movement of information in packets between two or more points is defined. The means outlined here could develop the optimal points of exchange between vehicles (or all moving communicators) for the maximum protection, greatest productivity, or shortest delays in a like fashion.

(9) A Blockchain is a data structure that can be timed-stamped and signed using a private key to prevent tampering. There is developed a consensus of authenticity between records that are each individually in agreement at a given time. As a distributed database, those records not in agreement at a given time are considered inauthentic. However, records change and distribution to all record holders is at variable delays. The chain may be thought of as an ESN network and the means described here could be used to assure that records are updated to all points in a synchronous or secure fashion.

Again, the concept is to control propagation of material, information, infection, intrusion, vehicles, by the contest between individual components of varying susceptibility to exchange and communicability while taking into account acceptable delays.

(10) Personal Internet. For a search engine (e.g. Google), or Related Functions like Augmented Reality labeling, Pinterest, create an ongoing hot list of topics most frequently searched for, appreciated, photographed and enjoyed (designate by thumbs up button), while sorting out items or categories (such as recommended or advertised selections) that you frequently rejected, thumb down or pass over in a list. This becomes a presorted personal and individual list of links—one's "Personal Internet" PI. It is a file that one owns privately and controls its dissemination.

One could compare one's PI with another's PI to look for common interests, common dislikes and areas of conflict. This can be done with, or without, revealing the contents of one's PI list. For example, if one has preferences that he would prefer to keep secret,—that is the type of approach-avoidance conflict that this concept is intended to manage.

One could also allow confidential analysis of one's PI to define words and concepts for the purposes of classification, e.g., via Myers-Briggs, MMPI test or similar personality classification. Additionally, one could use the above classification to create affinity groups, where new interests, products, services, and activities are suggested, based on others of similar affinity, or PI, or both.

Further one could divide a PI into public and private sections, and reveal your public side to social media in order to enable searching for others, who have your same likes, dislikes, temptations, avoidances and compatible personality types (usually not the same types). Also, one could create an ongoing—constantly updating PI for appearance preferences, through a selection of anonymous faces, selections, body types and identity with well-known individuals. In some instances, the information from the private sections can be revealed in stages. Like an onion, layers that an individual is most comfortable with are removed until a core is revealed. Such a scheme could be used in dating or other meeting sites.

FIG. 19A, and FIG. 19B illustrate exemplary possible system configurations. The more appropriate configuration will be apparent to those of ordinary skill in the art when practicing the present technology. Persons of ordinary skill in the art will also readily appreciate that other system configurations are possible.

FIG. 19A illustrates a conventional system bus computing system architecture 2000 wherein the components of the system are in electrical communication with each other using a bus 2005. Exemplary system 2000 includes a processing unit (CPU or processor) 2010 and a system bus 2005 that couples various system components including the system memory 2015, such as read only memory (ROM) 2020 and random access memory (RAM) 2025, to the processor 2010. The system 2000 can include a cache of high-speed memory connected directly with, in close proximity to, or integrated as part of the processor 2010. The system 2000 can copy data from the memory 2015 and/or the storage device 2030 to the cache 2012 for quick access by the processor 2010. In this way, the cache can provide a performance boost that avoids processor 2010 delays while waiting for data. These and other modules can control or be configured to control the processor 2010 to perform various actions. Other system memory 2015 may be available for use as well. The memory 2015 can include multiple different types of memory with different performance characteristics. The processor 2010 can include any general purpose processor and a hardware module or software module, such as module 1 2032, module 2 2034, and module 3 2036 stored in storage device 2030, configured to control the processor 2010 as well as a special-purpose processor where software instructions are incorporated into the actual processor design. The processor 2010 may essentially be a completely self-contained computing system, containing multiple cores or processors, a bus, memory controller, cache, etc. A multi-core processor may be symmetric or asymmetric.

To enable user interaction with the computing device 2000, an input device 2045 can represent any number of input mechanisms, such as a microphone for speech, a touch-sensitive screen for gesture or graphical input, keyboard, mouse, motion input, speech and so forth. An output device 2035 can also be one or more of a number of output mechanisms known to those of skill in the art. In some instances, multimodal systems can enable a user to provide multiple types of input to communicate with the computing device 2000. The communications interface 2040 can generally govern and manage the user input and system output. There is no restriction on operating on any particular hardware arrangement and therefore the basic features here may easily be substituted for improved hardware or firmware arrangements as they are developed.

Storage device 2030 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 2025, read only memory (ROM) 2020, and hybrids thereof.

The storage device 2030 can include software modules 2032, 2034, 2036 for controlling the processor 2010. Other hardware or software modules are contemplated. The storage device 2030 can be connected to the system bus 2005. In one aspect, a hardware module that performs a particular function can include the software component stored in a computer-readable medium in connection with the necessary hardware components, such as the processor 2010, bus 2005, display 2035, and so forth, to carry out the function.

FIG. 19B illustrates a computer system 2050 having a chipset architecture that can be used in executing the described method and generating and displaying a graphical user interface (GUI). Computer system 2050 is an example of computer hardware, software, and firmware that can be used to implement the disclosed technology. System 2050 can include a processor 2055, representative of any number of physically and/or logically distinct resources capable of executing software, firmware, and hardware configured to perform identified computations. Processor 2055 can communicate with a chipset 2060 that can control input to and output from processor 2055. In this example, chipset 2060 outputs information to output 2065, such as a display, and can read and write information to storage device 2070, which can include magnetic media, and solid state media, for example. Chipset 2060 can also read data from and write data to RAM 2075. A bridge 2080 for interfacing with a variety of user interface components 2085 can be provided for interfacing with chipset 2060. Such user interface components 2085 can include a keyboard, a microphone, touch detection and processing circuitry, a pointing device, such as a mouse, and so on. In general, inputs to system 2050 can come from any of a variety of sources, machine generated and/or human generated.

Chipset 2060 can also interface with one or more communication interfaces 2090 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 2055 analyzing data stored in storage 2070 or 2075. Further, the machine can receive inputs from a user via user interface components 2085 and execute appropriate functions, such as browsing functions by interpreting these inputs using processor 2055.

It can be appreciated that exemplary systems 2000 and 2050 can have more than one processor 2010 or be part of a group or cluster of computing devices networked together to provide greater processing capability.

For clarity of explanation, in some instances the present technology may be presented as including individual functional blocks including functional blocks comprising devices, device components, steps or routines in a method embodied in software, or combinations of hardware and software.

In some configurations the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims. Claim language reciting "at least one of" a set indicates that one member of the set or multiple members of the set satisfy the claim. Tangible computer-readable storage media, computer-readable storage devices, or computer-readable memory devices, expressly exclude media such as transitory waves, energy, carrier signals, electromagnetic waves, and signals per se.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A computer-implemented method comprising:
receiving a mixed group of computer files including files infected by malware and files not infected by malware;
processing, in a computer system, the mixed group of computer files based at least in part on persuasiveness parameters and susceptibility parameters, the processing including simulating a plurality of possible interactions of the mixed group of computer files based at least in part on the persuasiveness parameters and the susceptibility parameters;
based at least in part on the processing, splitting the mixed group of computer files into a first set of infected computer files and a second set of uninfected computer files;

comparing the first set of infected computer files to a first reference and the second set of uninfected computer files to a second reference;

in response to the comparing indicating a match, determining that a correct set of the persuasiveness parameters and the susceptibility parameters is found; and in response to the comparing indicating a mismatch, adjusting the persuasiveness parameters and the susceptibility parameters, and repeating the processing, the splitting, and the comparing.

2. The computer-implemented method of claim 1, wherein the processing, the splitting, and the comparing are repeated until at least one criteria is met.

3. The computer-implemented method of claim 1, wherein the persuasiveness parameters and the susceptibility parameters are adjusted prior to the repeating the processing, the splitting, and the comparing.

4. The computer-implemented method of claim 1, wherein the adjusting the persuasiveness parameters and the susceptibility parameters includes estimating changes for the persuasiveness parameters and the susceptibility parameters based at least in part on the comparing.

5. A system comprising:
a processor; and
a memory, having stored thereon a computer program executable by the processor, the computer program comprising a plurality of code sections for causing the processor to:
receive a mixed group of computer files including files infected by malware and files not infected by malware;
process, in a computer system, the mixed group of computer files based at least in part on persuasiveness parameters and susceptibility parameters, the processing including simulating a plurality of possible interactions of the mixed group of computer files based at least in part on the persuasiveness parameters and the susceptibility parameters;
based at least in part on the processing, split the mixed group of computer files into a first set of infected computer files and a second set of uninfected computer files;
compare the first set of infected computer files to a first reference and the second set of uninfected computer files to a second reference;
in response to the comparing indicating a match, determine that a correct set of the persuasiveness parameters and the susceptibility parameters is found; and
in response to the comparing indicating a mismatch, adjust the persuasiveness parameters and the susceptibility parameters, and
repeat the processing, the splitting, and the comparing.

6. The system of claim 5, wherein the processing, the splitting, and the comparing are repeated until at least one criteria is met.

7. The system of claim 5, wherein the persuasiveness parameters and the susceptibility parameters are adjusted prior to the repeating the processing, the splitting, and the comparing.

8. The system of claim 5, wherein the adjusting the persuasiveness parameters and the susceptibility parameters includes estimating changes for the persuasiveness parameters and the susceptibility parameters based at least in part on the comparing.

9. A non-transitory computer-readable medium, having stored thereon a computer program executable by a computing device, the computer program comprising a plurality of code sections for:
receiving a mixed group of computer files including files infected by malware and files not infected by malware;
processing, in a computer system, the mixed group of computer files based at least in part on persuasiveness parameters and susceptibility parameters, the processing including simulating a plurality of possible interactions of the mixed group of computer files based at least in part on the persuasiveness parameters and the susceptibility parameters;
based at least in part on the processing, splitting the mixed group of computer files into a first set of infected computer files and a second set of uninfected computer files;
comparing the first set of infected computer files to a first reference and the second set of uninfected computer files to a second reference;
in response to the comparing indicating a match, determining that a correct set of the persuasiveness parameters and the susceptibility parameters is found; and
in response to the comparing indicating a mismatch, adjusting the persuasiveness parameters and the susceptibility parameters, and repeating the processing, the splitting, and the comparing.

10. The non-transitory computer-readable medium of claim 9, wherein the processing, the splitting, and the comparing are repeated until at least one criteria is met.

11. The non-transitory computer-readable medium of claim 9, wherein the persuasiveness parameters and the susceptibility parameters are adjusted prior to the repeating the processing, the splitting, and the comparing.

12. The non-transitory computer-readable medium of claim 9, wherein the adjusting the persuasiveness parameters and the susceptibility parameters includes estimating changes for the persuasiveness parameters and the susceptibility parameters based at least in part on the comparing.

* * * * *